US00PP14092P39

(12) United States Plant Patent
Austin

(10) Patent No.: US PP14,092 P3
(45) Date of Patent: Aug. 26, 2003

(54) SHRUB ROSE PLANT NAMED 'AUSQUEST'

(75) Inventor: David C. H. Austin, Wolverhampton (GB)

(73) Assignee: David Austin Roses Limited, Wolverhampton (GB)

( * ) Notice: Subject to any disclaimer, the term of this patent is extended or adjusted under 35 U.S.C. 154(b) by 0 days.

(21) Appl. No.: 10/032,268

(22) Filed: Dec. 20, 2001

(65) Prior Publication Data

US 2003/0121078 P1 Jun. 26, 2003

(51) Int. Cl.[7] ..... A01H 5/00
(52) U.S. Cl. ..... Plt./102
(58) Field of Search ..... Plt./102, 103, 133, Plt./144, 104

(56) References Cited

PUBLICATIONS

UPOV–ROM GTITM Computer Database Mar. 2002, GTI Jouve Retrieval Software, Citation for Rosa 'Ausquest'.*

* cited by examiner

*Primary Examiner*—Bruce R. Campell
*Assistant Examiner*—June Hwu
(74) *Attorney, Agent, or Firm*—Klarquist Sparkman, LLP

(57) ABSTRACT

Shrub rose plant having a robust and very branching growth habit; large, rosette-shaped flowers, cupped at first, peals reflexing later having a soft apricot color, paling to pale cream on outer petals; and freely produced flowers at the ends of slightly arching stems.

1 Drawing Sheet

GENUS AND SPECIES

*Rosa hybrida.*

VARIETAL DENOMINATION

'AUSQUEST'.

SUMMARY OF THE INVENTION

The present invention relates to a new and distinct variety of rose plant of the shrub class which was originated by me by crossing an unnamed seedling, with the variety 'AUSgold', (U.S. Plant Pat. No. 8,688).

BACKGROUND OF THE INVENTION

The primary objective of this breeding was to produce a new rose variety having a very free-flowering and healthy plant with flowers of the classic English rose shape and with a good fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Robust and very branching shrub;
2. Large, rosette-shaped flowers, cupped at first, petals reflexing later;
3. Soft apricot color, paling to pale cream on outer petals; and
4. Freely produced flowers at the end of slightly arching stems.

Asexual reproduction of this new variety by budding on *Rosa dumetorum laxa* rootstock, as performed at Albrighton, England, shows that the foregoing and all other characteristics and distinctions come true to form and are established and transmitted through succeeding propagations.

COMPARISON WITH PARENTS

'AUSquest' differs from its seed parent in that the latter has rose pink flowers compared to 'AUSquests' apricot colored flowers and differs from its pollen parent which has rounded flowers as compared to 'AUSquest's' rosette-shaped flowers.

COMPARISON WITH SIMILAR VARIETY

'AUSquest' differs from 'AUSbaker' (U.S. Plant patent application Ser. No. 09/705,463, filed Nov. 2, 2000), the most similar variety, in that 'AUSquest' is broad and bushy with medium green foliage whereas 'AUSbaker' has a large, arching growth habit and has dark green foliage.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart, except where ordinary dictionary significance of color is indicated.

Parentage:

*Seed parent*.—Unnamed seedling (unpatented).

*Pollen parent*.—'AUSgold' (U.S. Plant Pat. No. 8,688).

FLOWER

Observations made from plants of 6 years of age grown in a garden environment at Albrighton, England.

Blooming habit: Recurrent.

Bud:

*Size*.—About 0.4 inches long when the petals start to unfurl.

*Form*.—The bud form is globular.

*Color*.—When sepals first divide, bud color is Yellow Group 4D. When half blown, the upper sides of the petals are White Group 155B; and the lower sides of the petals are Yellow Group 4D.

*Sepals*.—Color: Green Group 143A. Length: 0.8 inches. Width: 0.25 inches. Shape: Ovate with acuminate apex. Surface texture: Slightly hairy with serrated edges on appendaged sepals. There are three lightly appendaged sepals. There are two unappendaged sepals with hairy edges.

*Receptacle*.—Color: Yellow-Green Group 144A. Shape: Funnel. Size: Length: 0.4 inches; Width: 0.3 inches. Surface: Smooth.

*Peduncle*.—Length: Medium, averaging about 1.6–2.4 inches. Surface: Prickly. Color: Yellow-Green Group 144B. Strength: Erect.

Bloom:

*Size*.—Medium. Average open size is diameter is about 3.2 inches.

*Borne*.—Singly and in small, irregular clusters of up to four blooms.

*Stems*.—Strength: Arching. Average length is about 28–32 inches.

*Form*.—When first open: Globular with outer petals curled back. Permanence: Outer petals curl back.

*Petalage*.—Number of petals under normal conditions: 95–110.

*Color*.—The upper sides of the petals are White Group 155B. The reverse sides of the petals are White Group 155D. Both upper and reverse sides at the base are Yellow Group 10C. The major color on the upper side is White Group 155B, but the base color RHS 10C appears as blossom approaches its full open stage.

*Variegations*.—None.

*Discoloration*.—The general tonality at the end of the first day: Yellow-White Group 158B. As bloom ages color deepens to Yellow Group 10D with reddish spots.

*Fragrance*.—Moderate, with tea rose characteristics.

Petals:

*Average size*.—Length: 1.6 inches; Width: 1.2 inches.

*Texture*.—Smooth.

*Shape*.—Circular.

*Margin*.—Slight frill.

*Apex Shape*.—Rounded.

*Base shape*.—Goes to point.

*Form*.—Tips of outer petals slightly recurved, center petal edges slightly quill.

*Arrangement*.—Irregular.

*Petaloids*.—Number: 10. Color: Yellow Group 11C. Shape: Lanceolate.

*Persistence*.—Petals hang on and dry.

*Lastingness*.—On the plant: Long (seven days). As a cut flower: Not tested.

Reproductive parts:

*Anthers*.—Color: Yellow Group 12A. Arrangement: Tucked in calyx or partly so, mixed with petaloids.

*Filaments*.—Color: Yellow Group 4B.

*Pollen*.—Color: Yellow Group 8A.

*Pistils*.—Number: 40. Styles: Color: Green-Yellow Group 1C. Length: ½ inch. Stigmas: Color: Yellow Group 8A. Length: 1/32 inch.

*Hips*.—None produced.

Plant:

*Form*.—Shrub, English rose type.

*Growth*.—Vigorous.

*Mature plant*.—Height: 4 feet. Width: 3 feet.

*Rootstock*.—'Dr. Huey' recommended for United States.

Foliage:

*Number of leaflets on normal mid-stem leaves*.—5–7.

*Size*.—Medium (4.5 inches long×5.6 inches wide).

*Quantity*.—Normal.

*Color*.—New foliage: Upper side: Green Group 137B, red tint on edges. Lower side: Green Group 137D. Old foliage: Upper side: Green Group 139A. Lower side: Green Group 137A.

Leaflets:

*Size*.—About 2 inches long×1.6 inches wide.

*Shape*.—Round and pointed (cuspidate).

*Tip shape*.—Pointed.

*Base shape*.—Rounded.

*Texture*.—Semi-glossy.

*Edge*.—Serrated.

*Serrations*.—Small.

*Petiole color*.—Yellow-Green Group 146B.

*Petiole rachis*.—Color: Yellow-Green Group 144B. Underside: With prickles.

*Stipules*.—Length: 0.8 inches and serrated.

*Auricle shape, if present*.—Pointed.

*Disease resistance*.—Resistant to mildew, blackspot and rust under normal growing conditions.

*Pest resistance*.—Not tested.

Wood:

*New wood*.—Color: Yellow-Green Group 144B. Bark: Smooth.

*Old wood*.—Color: Yellow-Green Group 144A. Bark: Smooth.

Prickles:

*Quantity*.—On main canes from base: Ordinary. On laterals from main canes: Ordinary.

*Form*.—Hooked downward.

*Length*.—0.3 inch.

*Color when young*.—Yellow-Green Group 144C. Tip is Greyed-Purple Group 187C.

*Color when mature*.—Greyed-Red Group 181A.

Small prickles:

*Quantity*.—On main stalks: None. On laterals: None.

Climate hardiness: Hardy in Zones 4 to 9.

I claim:

1. New and distinct variety of rose plant of the shrub class, substantially as herein shown and described, characterized particularly by its robust and very branching growth habit; large, rosette-shaped flowers, cupped at first, petals reflexing later, having a soft apricot color, paling to pale cream on outer petals; and freely produced flowers at the ends of slightly arching stems.

* * * * *

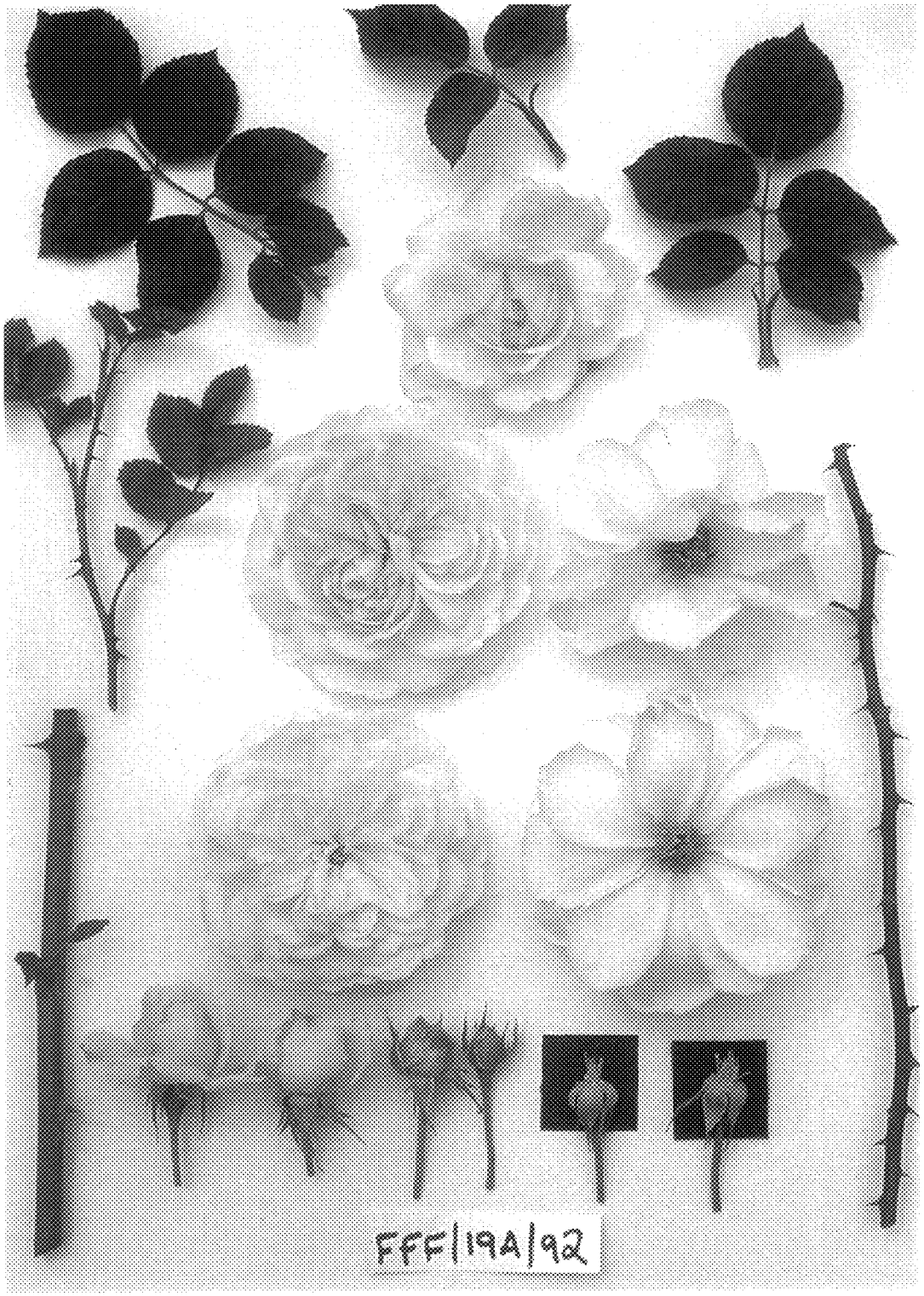
FFF/19A/92